United States Patent [19]

Fowler

[11] Patent Number: 4,781,041

[45] Date of Patent: Nov. 1, 1988

[54] APPARATUS FOR CLEANING GARMENTS AND SOFT GOODS CONTAMINATED WITH NUCLEAR, CHEMICAL AND/OR BIOLOGICAL CONTAMINANTS

[75] Inventor: David E. Fowler, Gainesville, Fla.

[73] Assignee: Quadrex Hps, Inc., Gainesville, Fla.

[21] Appl. No.: 923,770

[22] Filed: Oct. 27, 1986

Related U.S. Application Data

[62] Division of Ser. No. 679,641, Dec. 10, 1984.

[51] Int. Cl.$^4$ .............................................. D06F 43/08
[52] U.S. Cl. .................................. 68/18 F; 68/18 R; 252/626
[58] Field of Search ................... 8/137, 142; 210/756, 210/758, 764, 167; 68/18 R, 18 C, 18 F; 252/626, 630, 631; 134/109, 111

[56] References Cited

U.S. PATENT DOCUMENTS

| | | | |
|---|---|---|---|
| 2,660,869 | 12/1953 | McDonald | 68/18 R |
| 3,206,950 | 9/1965 | Xeros | 68/18 R X |
| 3,728,074 | 4/1973 | Victor | 68/18 C X |
| 4,235,600 | 11/1980 | Capella et al. | 68/18 R X |
| 4,443,269 | 4/1984 | Capella et al. | 252/626 X |
| 4,601,181 | 7/1986 | Privat | 68/18 F X |

FOREIGN PATENT DOCUMENTS 1408263 10/1975 United Kingdom .............. 68/18 C Primary Examiner—Philip R. Coe
Attorney, Agent, or Firm—Bernard A. Reiter; Mark G. Bocchetti

[57] ABSTRACT

Garments contaminated with radioactive, toxin, biological and/or chemical contaminants are deposited in a cleaning drum and the drum is agitated during a wash cycle. A dry cleaning solvent is added to the drum during the initial wash cycle and then drained to a distillation means. Within the distillation means, there is a neutralizing agent which deactivates the biological and toxin contaminants and chemically breaks down the chemical contaminants removed with the dry cleaning solvent from the cleaning drum. Dry cleaning solvent is then continuously added to the drum during the secondary wash cycle and continuously removed from the drum. After the dry cleaning solvent is removed from the drum, and before it is pumped back to the drum, the dry cleaning solvent is filtered to remove remaining trace particulate contaminants. The dry cleaning solvent is also passed through an adsorber where remaining trace chemical contaminants dissolves in the dry cleaning solvent are removed. The garments are then rinsed by circulating contaminant free dry cleaning solvent through the drum. After rinsing, the garments are dried by circulating hot, unsaturated dry cleaning solvent vapor through the drum.

18 Claims, 2 Drawing Sheets

APPARATUS FOR CLEANING GARMENTS AND SOFT GOODS CONTAMINATED WITH NUCLEAR, CHEMICAL AND/OR BIOLOGICAL CONTAMINANTS

This is a divisional application of U.S. patent application Ser. No. 06/679,641 filed on Dec. 10, 1984.

BACKGROUND OF THE INVENTION

1. Field of the Invention

The present invention relates generally to apparatus for decontaminating garments and soft goods, and more specifically, to the removal of radioactive particulate matter, chemical agents, toxins and/or biological agents as well as regularly encountered soiling materials from garments or other items of cloth, paper and rubber.

2. Brief Description of the Prior Art

A patent which purports to teach a method of decontaminating radioactive garments through the use of a dry cleaning solvent is U.S. Pat. No. 3,728,074. This system depends entirely on the filtration of nuclear particulates from the dry cleaning solvent as the dry cleaning solvent is circulated through the contaminated garments. Therefore, since the radioactive particulates are captured entirely by the filters, it is presumably necessary to replace those filters often. Also, this system operates under positive pressure and includes an expansion bag. Any leak in the system or rupture of the expansion bag will result in radioactive particulates being discharged to the atmosphere.

There is also in the prior art a method which seems to teach the cleaning of radioactive particulate material from industrial workers protective clothing through the use of a conventional laundry wash. This wash entails a standard 30 to 45 minute water washing using commercial detergent followed by a separate drying cycle of usually 60 minutes in a conventional hot air or other type textile clothes dryer. This system although effective in producing a clean looking garment, normally is so inefficient that from 20 to 35% of the clothing must be rewashed because insufficent radioactivity has been removed to permit reuse of the protective article. Moreover, this method generates quantities of radioactivity contaminated wash water which must be diluted to safe concentrations before it is release or evaporated to a concentrate and then drummed and buried in an radiation waste burial facility. This makes the method very costly and time consuming.

There is little in the prior art dealing with the removal of chemicals or toxins such as pesticides and chemical warfare agents such as tabun, sarin, soman or mustard gas from articles of protective clothing. This is also the case with garments contaminated with biological contaminants. The military currently decontaminates protective articles contaminated with chemical agents through the use of high temperature steam. Although the article is decontaminated of chemical agents in this manner, it is also usually no longer suitable for reuse. Also, this method does noting to deactivate or destroy the agent.

Accordingly, it is an object of the present invention to provide apparatus for decontaminating garments contaminated with radioactive particulates which dislodges such radioactive particulates by using a dry cleaning solvent.

Another object of the present invention is to provide apparatus which captures and contains radioactive, chemical and biological contaminants removed from the garments.

A further object of the present invention is to provide apparatus for decontaminating radioactively contaminated garments in a single apparatus which also serves to dry the garments after completion of the wash cycle.

Another object of the present invention is to provide apparatus for decontaminating garments contaminated with pesticides and chemical agents such as those used in chemical warfare (e.g. HD, GD, GA, GB).

Further, it is an object of the present invention to provide apparatus for decontaminating garments contaminated with biological and toxin contaminants including anthrax, salmonella, botulinum, a mycotoxin commonly referred to as yellow rain and other viruses and bacteria which can be potentially used in warfare or terrorist activity.

A further object of the present invention is to provide apparatus for decontaminating garments which limits the amount of contaminated waste generated.

Further, it is an object of the present invention to provide apparatus which is self contained and relatively easy to transport so that it may be taken from site to site.

Another object of the present invention is to provide apparatus which operates under negative pressure so that, should leaks develop, no contaminants will be discharged to the atmosphere.

A further object of the present invention is to provide apparatus for decontaminating garments having radioactive, chemical and biological contamination in a quick and efficient manner.

Further, it is an object of the present invention to provide apparatus which can be operated on a continuous basis for relative long periods.

Briefly stated, the foregoing and numerous other features, objects and advantages of the present invention will become readily apparent upon reading the detailed description, claims and drawings set forth hereinafter. These features, objects and advantages are accomplished by circulating a dry cleaning solvent through the articles to be decontamintated while the articles are being agitated so that particulate and chemical contaminants which may be radioactive, chemical and/or biological in nature may be dislodged or dissolved and removed from the garments.

After an initial wash cycle, the dry cleaning solvent containing suspended particulate and dissolved contaminants is dumped from the drum housing which provides agitation to the garments, into a distillation means. Chemical agents including pesticides and nerve, blister, and other incapacitating or killing agents such as sarin and mustard are also removed from the garments during this initial wash cycle because they are all highly soluble in the dry cleaning solvent, preferably trichlorotrifluoroethane referred to herein as the solvent.

Located in the distillation means is a neutralizing agent which serves to deactivate biological contaminants, chemically break down chemical contaminants to nontoxic or less toxic substances and to prevent the migration of chemical contaminants with the solvent while the distilling is being performed. During the second phase of the wash cycle, an initially contaminate free volume of dry cleaning solvent is continuously circulated through the agitating drum housing in which the contaminated garments are placed in a closed loop arrangement. The closed loop includes a filter for the removal of additional particulates dislodged from the garments and an adsorber which preferentially adsorbs chemical agents which have been dissolved in the dry cleaning solvent during this phase of the wash cycle.

Between the second phase of the wash cycle and the drying cycle, there is a rinse cycle. Residual solvent adsorbed in the garments is extracted by pumping a quantity of clean solvent through the drum thereby rinsing the garments of the residual solvent.

During the drying phase, hot solvent vapor is circulated through the drum housing in closed loop fashion by a fan. A portion of the hot solvent vapor being circulated is run through a condenser and returned to the fan so that the vapor being circulated through the drum housing is not saturated thereby facilitating more rapid drying.

Solvent vapor generated in the distillation means is collected and condensed and returned to the secondary solvent tank in pure liquid phase.

In other words, the invention comprises the use of a drum housing similar to that used in conventional dry cleaning systems and the use of trichlorotrifluoroethane as the dry cleaning solvent. The solvent not only serves to dislodge contaminating particulate matter, but also solubilizes various pesticides and chemical agents used in chemical warfare. The contaminated solvent is then drained from the drum housing to a distillation means which serves a dual function. The first function of the distillation means is to distill pure solvent from the contaminated solvent dumped therein while the second function of the distillation means is to serve as a container for a neutralizing agent which destroys or deactivates both chemical and biological contaminants. The neutralizing agent is comprised of a mixture of calcium hypochlorite or sodium hypochlorite and sodium hydroxide or potassium hydroxide. The concentration of calcium or sodium hypochlorite must be greater than 10% and the concentration of sodium hydroxide or potassium hydroxide must be greater than 1.0 Normal.

The biological contaminants coming in contact with this neutralizing agent are destroyed. The chemical contaminants coming in contact with this neutralizing agent are chemically broken down to either nontoxic or less toxic substances. The density of the neutralizing agent is less than the density of solvent and further the neutralizing agent is nonmiscible in solvent, because the neutralizing agent has a polar chemical configuration. Therefore, the neutralizing agent will float as a layer on top of any solvent dumped to the distillation means. Any chemical agent attempting to migrate from the distillation means with the solvent vapor must first pass through this layer of neutralizing agent. Upon contacting the neutralizing agent layer, the chemical contaminants are broken down to heavier components which settle out in the distillation means assuring that no contaminants migrate from the distillation means with the solvent vapor. The solvent vapor this generated is then condensed and collected and placed in readiness for the next wash load.

Given the relatively small size required for the apparatus, making it not unreasonable to transport, and that washings may be performed consecutively, the invention is particularly adaptable to use by the military for decontaminating the protective garments of soldiers, and the like, at or near the place of battle.

Garments currently used by the military for protection against chemical warfare contain a layer of activated carbon which serves to adsorb any chemical agents coming in contact with the garment thereby preventing the chemical agents from contacting the wearer of the garment. Since there is currently no effective or efficient method of stripping off chemical agents adsorbed by the activated carbon impregnated in the garment, once the garment becomes contaminated, it must be replaced. The invention disclosed herein allows the activated carbon contained in the garment to be cleaned of chemical agents and therefore be reused.

The entire wash and dry cycle of the present invention can be performed in less than 45 minutes. Thus, it is entirely feasible that mobile dry cleaning decontamination units can be used in battle field conditions to regenerate the protective quality of the garments worn under those type of conditions.

DESCRIPTION OF THE PREFERRED EMBODIMENT

Figure 1:
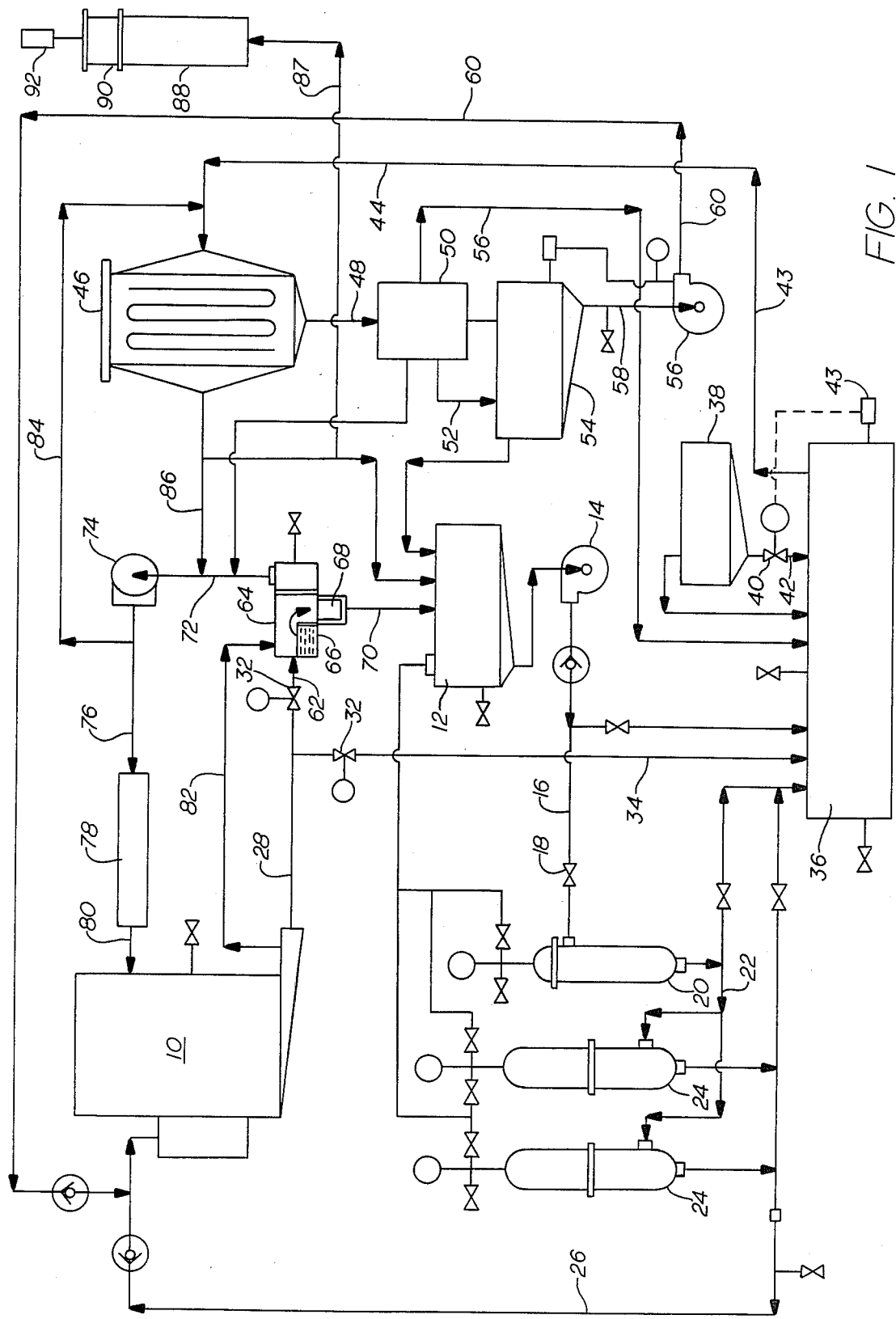
FIG. 1 is a flow diagram and schematic view of the apparatus constructed according to the present invention.

Turning first to FIG. 1, there is shown a schematic illustration of a dry cleaning system constructed according to the present invention. Such arrangement is unique in its ability to remove and contain multiple forms of contamination as well as in its ability to render inactive many contaminants otherwise harmful to human life.

The dry cleaning apparatus of this invention includes a rotatable cleaning cage or drum 10 wherein garments contaminated with radioactive particulate matter, toxin contaminants, chemical contaminants and/or biological contaminants. The chemical contaminants may be pesticides or those types of nerve agents and blister agents used by the military in chemical warfar. They include: HD (mustard gas), GD, GA, GB and VX. The types of biological or toxin contaminants encountered may include salmonella, botulinum, anthrax and a mycotoxin commonly referred to as yellow rain.

The garments are cleaned in the drum 10 by placing within drum 10 an initial charge of dry cleaning solvent and agitating the garments by imparting to drum 10 a rotational movement of alternating direction. This action coupled with the garments submersion in the dry cleaning solvent, trichlorotrifluoroethane, serves to loosen and dislodge particulate contaminants and dissolve the chemical contaminants. The dry cleaning solvent is supplied by primary solvent tank 12 in fluid communication with drum 10. A pump 14 is used to force the solvent from the primary solvent tank 12 through conduit 16, isolation valve 18, bag filter 20, conduit 22, adsorbers 24, conduit 26 and into the top of drum 10.

This initial wash phase consists of a closed loop agitation with a finite quantity of solvent. Before beginning the secondary wash phase, the initial wash phase may be repeated one or more times. This reiteration of cycles may be accomplished by manual or automatic control.

Disposed in the bottom of drum 10 is an outlet conduit 28 which permits withdrawal of the dry cleaning solvent together with any radioactive particulate matter, chemical agents and/or biological and toxin agents removed from the garments during the wash cycle. At the completion of the initial wash cycle, motorized ball 30 opens allowing drum 10 to drain and the solvent and contaminants are communicated through conduit 28, motorized ball 30 and conduit 34 to still tank 36. Also, at the conclusion of the initial wash cycle, an extract motor imparts to drum 10 a rapid, one directional, spin to aid in draining the contaminated solvent from drum 10. Most of the contaminants (approximately 93%) are removed by the initial phase of the wash cycle. For heavily contaminated garments, it may be necessary to repeat the initial phase of the wash cycle.

Contained within still tank 36 is an approximately 2" thick layer of neutralizing agent comprising a mixture of concentrated bleach and caustic having a pH of approximately 12. The neutralizing agent can be made by starting with a quantity of water as a base and adding to the water either calcium hypochlorite or sodium hypochlorite to create at least a 10% solution of either. Then dissolve solid sodium hydroxide or potassium hydroxide in the concentrated bleach solution so that the solution has at least a 1.0 Normal hydroxide present. The neutralizing agents are introduced to still tank 36 from a neutralizing agent tank 38 through a motorized ball valve 40 and a conduit 42. Motorized ball valve 40 is operated by level controller 43 so that a minimum 2" thick layer of neutralizing agent is present in still tank 36 at the beginning of each wash. These neutralizing agents are not miscible with the dry cleaning solvent because they are polor in chemical configuration and therefore, the layer of neutralizing agents will float on top of the solvent and contaminants flushed from drum 10 and into still tank 36.

Still tank 36 is maintained at a temperature of approximately 118° F. which is the boiliing point of trichlorotrifluoroethane. As the solvent boils within the still tank 36, the resulting vapor must first pass through and thereby contact the layer of neutralizing agent riding on top of the liquid solvent. Any chemical agents attempting to migrate with the solvent vapor will be chemically oxidized by the neutralizing agent and will ultimately end up as residue on the bottom of the still tank 36 in a much less toxic form after distillation is complete. The neutralizing agents also serve to destroy the biological and toxin contaminants. It is important that no contaminants be permitted to migrate with the solvent vapor from the still tank 36 as this would cause a recontamination of the garments during a later phase of the process and could also create a vapor hazard to the operator when he opens drum 10 at the completion of the cycle. Note that the agents used in chemical warfare can kill even in the parts per million range.

The resulting contaminant free solvent vapor is then communicated by convection through Viton lined conduit 44 to condenser 46. Condensate generated by condenser 46 is communicated through conduit 48 to water separator 50 by gravity. The solvent is then communicated through conduit 52 to secondary solvent tank 54. Water separated from the dry cleaning solvent by water separator 50 is communicated through conduit 56 to the still tank 36 so as to eliminate moisture contamination of the now clean solvent generated by distillation.

During the secondary phase of the wash cycle, motorized ball 30 closes and motorized ball 32 opens and pump 14, again taking suction from primary solvent tank 12, pumps solvent in a continuous fluid circuit comprised of pump 14, conduit 16, bag filter 20, conduit 22, adsorbers 24, conduit 26, drum 10, conduit 28, motorized ball valve 32, conduit 62, liquid level control structure 64, conduit 70 and back to primary solvent tank 12. During the secondary phase of the wash cycle, as in the initial phase, movement to drum 10 is imparted by the wash motor generating a rotational movement of alternating direction.

As the solvent flows through filter 20, particulate contaminants, both radioactive and biological in nature, are removed from the solvent. Similarly, chemical contaminants dissolved in the solvent are adsorbed in adsorbers 24. The preferred adsorbent is Fullers Earth, but it is also possible to use activated silica, activated alumina, activated carbon or diatomaceous earth as the adsorbent. Uncontaminated solvent enters drum 10 dislodging particulate contaminants not removed during the initial wash cycle and dissolving chemical contaminants not dissolved during the initial wash cycle. A level of liquid solvent in drum 10 is maintained by liquid level control structure 64 which contains a weir 66 so situated so as to maintain the desired level.

There are weep holes at the base of weir 66 so that all dry cleaning solvent may be drained from drum 10 when pump 14 is de-energized at the completion of the secondary phase of the wash cycle. Before exiting the liquid level control structure 64, the dry cleaning solvent must first pass through macro particle separator 68 thereby removing gross particulate contaminants from the dry cleaning solvent. From the macro particle separator 68 the dry cleaning fluid is transmitted via conduit 70 to primary solvent tank 12 thus completing a continuous fluid circuit.

In an alternative arrangement, macro particle separator 68 could be located immediately after drum 10 and before motorized ball 30 and 32 and serve the identical function while also protecting motorized ball 30 and 32 from being plugged with debris flushed from drum 10.

At the completion of the secondary phase of the wash cycle, the wash motor is de-energized and the extract motor is re-energized. The resulting rapid spinning of drum 10 aids in the removal of liquid solvent from the drum and adsorbed in the garments. Clean solvent is then transmitted to drum 10, via conduit 60 by pump 56 taking suction from secondary solvent tank 54 via conduit 58. The clean solvent is pumped to drum 10 in the manner described above, then drained from drum 10 via conduit 28 into primary solvent tank 12 while the extract motor is operating in order to facilitate a rinse cycle thereby insuing that no contaminants remain on the garments or within the drum 10.

During the drying stage of operation, fan 74 is energized. Fan 74 takes solvent vapor from liquid level control structure 64 via plenum 72 and transmits that solvent vapor through duct 76, heater 78, duct 80, drum 10, duct 82 and back to liquid level control structure 64, thus completing a continuous vapor circuit. The function of heater 78 is to heat the solvent vapor entering drum 10 to facilitate the drying of the garments contained in drum 10 by causing the evaporation of any liquid solvent remaining in drum 10.

There is a side stream continuous vapor circuit also originating with fan 74. In this side stream continuous vapor circuit, fan 74 circulates solvent vapor through duct 76, line 84, condenser 46, conduit 86, conduit 72 and back to fan 74. The purpose of circulating this side stream through condenser 46 is to desaturate the solvent vapor being circulated through drum 10. Thus, the liquid solvent remaining in drum 10 is continuously evaporated by the passage of hot, unsaturated solvent vapor through drum 10, thereby drying the garments within.

In an alternative embodiment, all of the vapor being circulated through the drum 10 during the drying cycle could also be circulated through the condenser 46. This would desaturate the entire vapor stream being circulated and, therefore, dry would be accomplished more rapidly. However, this alternative embodiment would require greater energy consumption.

There is a pressure equalization system connected to primary solvent tank 12 comprised of conduit 87, carbon column 88, HEPA filter 90 and solenoid valve 92. At the very onset of operation of the process, when pump 14 is actuated and begins pumping dry cleaning solvent from primary solvent tank 12, the pumping of the dry cleaning solvent will cause some vaporization of the dry cleaning solvent meaning that there will be some gaseous expansion within the system. Therefore, simultaneously with the actuation of pump 14, solenoid valve 92 opens. This allows air and dry cleaning solvent vapor to flow through conduit 87 and into carbon column 88 where the solvent vapor and any trace quantities of chemical agent are adsorbed by the activated carbon. The high efficiency particulate air filter 90 prevents the escape of particulate contaminants to the atmosphere. Filter 90 is designed to remove 99.97% of all particles greater than 0.3 microns in size. Therefore, what actually escapes to the atmosphere through solenoid valve 92 is the air that was originally contained within the system and most if not all of the air is expelled during the brief time (approximately 15 seconds) that solenoid valve 92 remains open.

When condenser 46 begins condensing solvent vapor received from still tank 36, a partial vacuum within the system is created and from that point on, the entire process is operated under a partial vacuum. Operating under a partial vacuum yields a number of advantages to the invention. First, the rate of distillation in still tank 36 is enhanced. Second, the time required for the drying cycle is shortened. Third, should the apparatus develop any leaks, those leaks will cause atmosphere to flow into the apparatus rather than contaminants to flow into the atmosphere thus obviating the escape of toxic or hazardous materials.

When the process has been run through completion, the door to drum 10 cannot be opened without first equalizing the pressure within and without the apparatus. Therefore, solenoid valve 92 is again actuated, opening for a brief period. Air is allowed to rush back into the system through solenoid valve 92, hepa filter 90 and carbon column 88. As the air flows across carbon column 88, solvent adsorbed therein is stripped off thereby partially regenerating the activated carbon.

Figure 2:
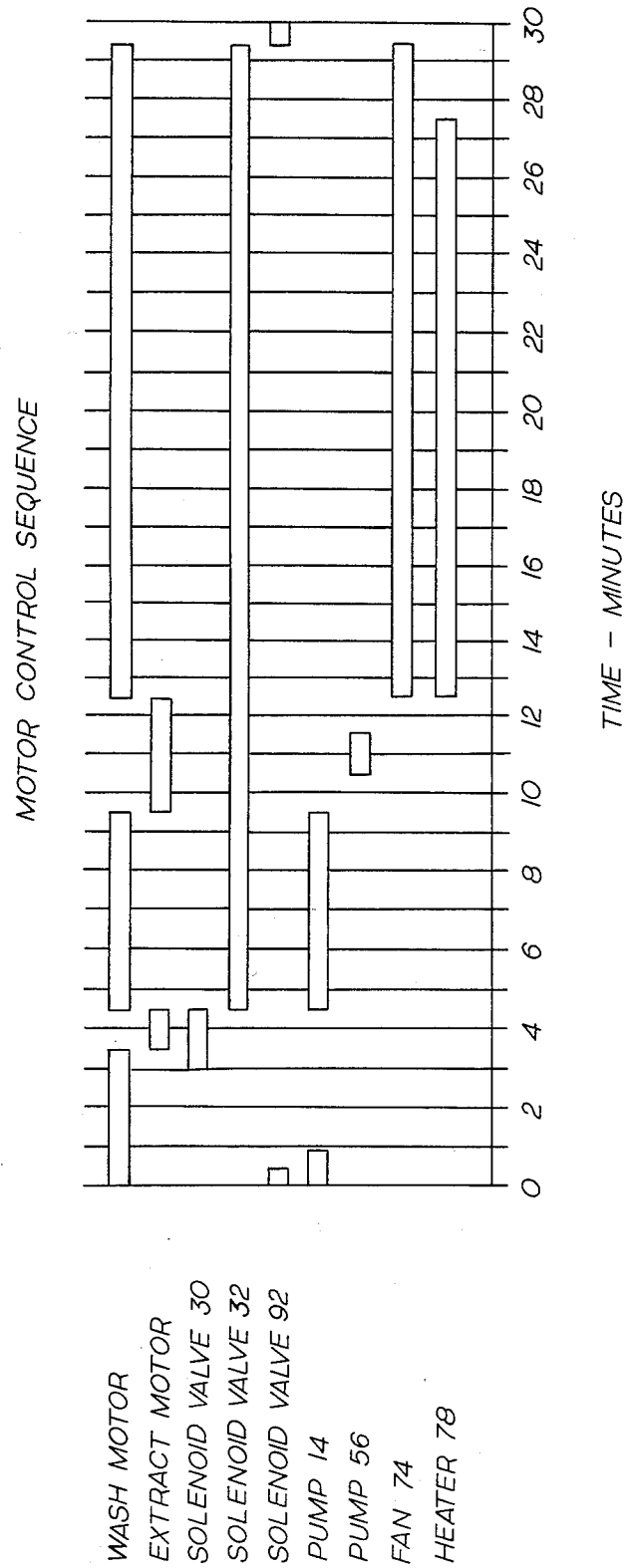
FIG. 2 is a diagram showing the sequence of operations of the parts of the invention during the wash and dry cycles.

FIG. 2 shows a motor control sequence for automatically actuated equipment used in the apparatus once operation is started. Review of FIG. 2 in conjunction with FIG. 1 will promote a better understanding of the order of operation of the process.

First, contaminated garments are placed in the drum 10. Pump 14, solenoid valve 92 and the wash motor to drum 10 are simultaneously actuated with solenoid valve 92 remaining opened for only a brief period and pump 14 remaining energized long enough to place an initial charge of cry cleaning solvent within drum 10. Shortly before (15 seconds) the completion of the initial phase of the wash cycle, motorized ball valve 30 opens thereby beginning the draining of drum 10. At the completion of the initial phase of the wash cycle, the wash motor of drum 10 is de-energized and the extract motor is energized thereby facilitating additional draining of drum 10 through motorized ball valve 30. After approximately 30 seconds, the extract motor de-energizes and the wash motor re-energizes. Also, at this point, motorized ball valve 30 closes and motorized ball valve 32 opens and pump 14 re-energizes. Pump 14 is now pumping dry cleaning solvent in a closed fluid circuit originating and ending with primary solvent tank 12. As the dry cleaning solvent is continously circulated through drum 10, bag filter 20 and adsorbers 24, the remaining trace contaminants not removed in the initial phase of the wash cycle, are thus removed in this seocndary phase of the wash cycle. At the completion of the secondary phase of the wash cycle, the wash motor and pump 14 de-energize and the extract motor to drum 10 re-energizes to facilitate the draining of the solvent remaining in drum 10 to primary solvent tank 12. One minute later, pump 56 begins pumping uncontaminated solvent from secondary solvent tank 54 through drum 10 which in turn drains to primary solvent tank 12. This is, in essence, a rinse cycle. At the completion of the rinse cycle, the quantity of solvent contained within primary solvent tank 12 is at its original level. At the completion of the rinse cycle, the extract motor to drum 10 de-energizes and the wash motor re-energizes. Also, at this point, fan 74 and heater 78 energize thus beginning the drying phase of the process. The heater 78 will de-energize shortly before the fan 74, allowing cool solvent vapor to be circulated through drum 10 thus cooling the garments. At the completion of the drying phase of the process, the wash motor to drum 10 and the fan 74 will de-energize and the motor operated ball valve 32 closes. Simultaneously, solenoid valve 92 opens thereby equalizing the pressure within and without the system.

At this point, drum 10 may be opened and the garments removed. Also, distillation within still tank 36 is complete and therefore, the quantity of solvent contained in secondary solvent tank 54 has been returned to its original level. Thus, the apparatus is immediately ready to receive another load of contaminated garments.

It should be noted that an alternate embodiment could be practiced which does not contain the still tank 36. In such case, the garments would be cleaned by continously circulated solvent through the bag filter 20, adsorbers 24 and drum housing 10. However, in such an embodiment, since the bag filter 20 and the adsorbers 24 would be required to remove all of the contaminants, they would have to be sized much larger and would have to be replaced frequently.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. An apparatus for decontaminating garments contaminated with radioactive, toxin, biological and/or chemical contaminants comprising:

(a) a drum for supporting the contaminated garments;
(b) a pump for placing an initial charge of dry cleaning solvent in which the chemical contaminants are soluble within said drum during an initial wash cycle;
(c) means for draining said drum of the dry cleaning solvent with suspended particulate contaminants and dissolved chemical contaminants at the completion of the initial wash cycle;
(d) a primary solvent tank in fluid communication with said pump to supply said pump with dry cleaning solvent;
(e) a separate and distinct container into which said drum may be drained of contaminated solvent at the completion of the initial wash cycle;
(f) means for continuously circulating the dry cleaning solvent through said drum to remove additional contaminants during a secondary wash cycle;
(g) filtering means for continuously removing radioactive and/or biological particulate matter suspended in the solvent being continously circulated during the secondary wash cycle;
(h) adsorber means for continuously removing chemical contaminants dissolved in the solvent being continuously circulated during the secondary wash cycle.

2. An apparatus as recited in claim 1, wherein said separate and distinct container is a distillation means for distilling the contaminated dry cleaning solvent drained from said drum so that the dry cleaning solvent is vaporized by said distillation means while the contaminants remain in liquid or solid phase.

3. An apparatus as recited in claim 2, further comprising:
(a) a condenser to condense the dry cleaning solvent vapor generated by said distillation means;
(b) a neutralizing agent contained within said distillation means which destroys or deactivates chemical, toxin and/or biological contaminants and prevents the migration of chemical contaminants with the dry cleaning solvent vapor generated by said distillation means to said condenser;
(c) a water separator means to separate water from dry cleaning solvent condensed within said condenser;
(d) a second tank in fluid communication with said water separator and said condenser to receive pure dry cleaning solvent condensed by said condensing means with water removed by said water separator means.

4. An apparatus as recited in claim 3, wherein said neutralizing agent is a minimum 10% solution of calcium hypochlorite in water containing at least 1.0 N hydroxide by dissolving one member of the following group in said calcium hypochlorite solution:
(a) sodium hydroxide; and
(b) potassium hydroxide.

5. An apparatus as recited in claim 3, wherein said neutralizing agent is a minimum 10% solution of sodium hypochloride in water containing at least 1.0 N hydroxide by dissolving one member from the following group in said sodium hypochlorite solution:
(a) sodium hydroxide; and
(b) potassium hydroxide.

6. An apparatus as recited in claim 3, wherein said dry cleaning solvent is trichlorotrifluoroethane.

7. An apparatus as recited in claim 6, wherein said adsorber means uses an adsorbent selected from the group consisting of:
(a) Fuller's Earth;
(b) activated alumina;
(c) activated carbon;
(d) silica gel; and
(e) diatomaceous earth.

8. An apparatus for decontaminating garments contaminated with radioactive, toxin, biological and/or chemical nerve and blister agent contaminants comprising:
(a) a drum for supporting the contaminated garments during a wash cycle and a dry cycle;
(b) means for circulating dry cleaning solvent through said drum to flush away any radioactive, toxin and/or biological particulate material and/or chemical nerve and blister agent contaminants separated from the garments out of the drum during the wash cycle with a dry cleaning solvent;
(c) a distillation means for separating the dry cleaning solvent from the contaminants, said distillation means receiving dry cleaning solvent and contaminants from said drum;
(d) an initial charge of a neutralizing agent contained within said distillation means, said neutralizing agent rendering nontoxic any biological, toxin, and chemical nerve and blister agent contaminants on contact;
(e) adsorber means for continuously removing chemical contaminants dissolved in the solvent as separated from the garment during the wash cycle so that before the dry cleaning solvent is returned to said drum by said means for continuously circulating, the dry cleaning solvent is cleansed of dissolved chemical contaminants.

9. An apparatus as recited in claim 8, wherein said neutralizing agent is nonmiscible with said solvent and floats as a contiguous layer above the solvent in said distillation means so that any vapor generated in said distillation means must pass through said neutralizing agent means thereby preventing the migration of any chemical nerve and blister agent contaminants with said solvent vapor from said distillation means.

10. An apparatus for decontaminating garments and/or soft goods contaminated with radioactive particulates, toxins such as yellow rain, biological agents such as salmonella, botulinum and anthrax, and chemical nerve and blister agents such as tabun, soman, sarin and mustard comprising:
(a) a drum means in which contaminated garments and/or soft goods are washed with a dry cleaning solvent to remove the radioactive, toxin, biological and/or chemical contaminants;
(b) means for draining said dry cleaning solvent from said drum means;
(c) a distillation means receiving said dry cleaning solvent from said drum means via said means for draining;
(d) a layer of neutralizing agent in said distillation means, said layer of neutralizing agent rendering nontoxic the toxin, biological and/or chemical contaminants dissolved or suspended in said dry cleaning solvent on contact.

11. An apparatus as recited in claim 10 further comprising:
(a) a solvent tank for holding said dry cleaning solvent purified in said distillation means;

(b) a pump for transmitting said dry cleaning solvent from said solvent tank to said drum means.

12. An apparatus as recited in claim 11 further comprising:
a filter means for removing particulate contaminants including the radioactive particulates and biological agents from said dry cleaning solvent before said dry cleaning solvent is transmitted to said drum means.

13. An apparatus as recited in claim 11 further comprising:
adsorber means for removing any traces of chemical nerve and blister agent contaminants from said dry cleaning solvent before said dry cleaning solvent is transmitted to said drum means.

14. An apparatus as recited in claim 13 wherein:
said adsorber means uses an adsorbent selected from the group consisting of:
(a) fuller's earth;
(b) activated alumina;
(c) activated carbon;
(d) silica gel;
(e) diatamaceous earth.

15. An apparatus as recited in claim 10 wherein:
said layer of neutralizing agent is a mixture of an aqueous solution of concentrated bleach and caustic.

16. An apparatus as recited in claim 15 wherein:
said dry cleaning solvent is trichlorotrifluoroethane.

17. An apparatus as recited in claim 10 wherein:
said neutralizing agent is a minimum ten percent (10%) solution of calcium hypochlorite and water containing at least 1.0 Normal hydroxide obtained by dissolving one member of the following group in said calcium hypochlorite solution:
(a) sodium hydroxide; and
(b) potassium hydroxide.

18. An apparatus as recited in claim 10 wherein:
said layer of neutralizing agent is a minimum ten percent (10%) solution of sodium hypochlorite and water containing at least 1.0 Normal hydroxide obtained by dissolving one member of the following group in said sodium hypochlorite solution;
(a) sodium hydroxide; and
(b) potassium hydroxide.

* * * * *